(12) United States Patent
Suzuki

(10) Patent No.: US 7,976,552 B2
(45) Date of Patent: Jul. 12, 2011

(54) LIGATION APPARATUS

(75) Inventor: Keita Suzuki, Tokyo (JP)

(73) Assignee: Olympus Corporation, Tokyo (JP)

( * ) Notice: Subject to any disclaimer, the term of this patent is extended or adjusted under 35 U.S.C. 154(b) by 866 days.

(21) Appl. No.: 10/881,487

(22) Filed: Jun. 30, 2004

(65) Prior Publication Data

US 2005/0033312 A1 Feb. 10, 2005

(30) Foreign Application Priority Data

Jul. 2, 2003 (JP) ................................ 2003-270527

(51) Int. Cl.
*A61B 17/115* (2006.01)
*A61B 17/22* (2006.01)

(52) U.S. Cl. ........................................ 606/144; 606/142

(58) Field of Classification Search .................. 606/110, 606/75, 179, 205, 139–144; 227/175.1, 178.1, 227/180.1

See application file for complete search history.

(56) References Cited

U.S. PATENT DOCUMENTS

| | | | | |
|---|---|---|---|---|
| 3,989,049 A | * | 11/1976 | Yoon | 128/831 |
| 5,015,249 A | * | 5/1991 | Nakao et al. | 606/142 |
| 5,026,379 A | * | 6/1991 | Yoon | 606/141 |
| 5,156,609 A | | 10/1992 | Nakao et al. | |
| 2002/0198537 A1 | | 12/2002 | Smith et al. | |

FOREIGN PATENT DOCUMENTS

| | | |
|---|---|---|
| EP | 0 432 560 A2 | 6/1991 |
| EP | 0 609 612 A2 | 8/1994 |
| JP | 5-184535 | 7/1993 |
| JP | 5-74508 | 10/1993 |
| JP | 8-280701 | 10/1996 |

* cited by examiner

*Primary Examiner* — Anhtuan T Nguyen
*Assistant Examiner* — Amy Lang
(74) *Attorney, Agent, or Firm* — Scully, Scott, Murphy & Presser, P.C.

(57) ABSTRACT

A ligation apparatus includes an insertion tube extending toward one direction, a clamp part which is provided on a distal side of the insertion tube and clamps a living organ, a first control mechanism which is connected to the clamp part via a first control shaft member inserted inside the insertion tube and controls opening-and-closing action of the clamp part by advancing and retracting the first control shaft member, a ligation part which ligates the living organ by closing a pair of arm members provided on the distal side of the insertion tube; and a second control mechanism which is connected to the ligation part via a second control shaft member inserted inside the insertion tube, and closes the pair of arm members and releases the ligation part by advancing and retracting the second control shaft member.

13 Claims, 11 Drawing Sheets

LIGATION APPARATUS

BACKGROUND OF THE INVENTION

Priority is claimed on Japanese Patent Application No. 2003-270527, filed Jul. 2, 2003, the content of which is incorporated herein by reference.

FIELD OF THE INVENTION

The present invention relates to a ligation apparatus which performs ligation of an affected part by inserting it into a living organ.

DESCRIPTION OF RELATED ART

Conventionally, a ligation apparatus which performs ligation of an affected part of a living organ such as a blood vessel, etc., by making plastic deformation of a clip made of metal or resin, has been used for a treatment with an endoscope. As for this kind of ligation apparatus, one holding the clip on its distal end and inserted into a canal of the endoscope is proposed (for example, refer to FIG. 1 of Japanese Utility Model Application No. Hei 5-74508, and FIG. 1 of Japanese Unexamined Patent Application, First Publication No. Hei 8-280701).

SUMMARY OF THE INVENTION

A ligation apparatus of the present invention includes: an insertion tube extending in one direction; a clamp part which is provided on a distal side of the insertion tube and clamps a living organ; a first control mechanism which is connected to the clamp part via a first control shaft member inserted inside the insertion tube and controls opening-and-closing action of the clamp part by advancing and retracting the first control shaft member; a ligation part which ligates the living organ by closing a pair of arm members provided on the distal side of the insertion tube; and a second control mechanism connected to the ligation part via a second control shaft member inserted inside the insertion tube, which closes the pair of arm members and releases the ligation part by advancing and retracting the second control shaft member.

A control tube inserted inside the insertion tube may be further included; and the second control shaft member may be inserted inside the control tube so that the second control shaft member freely moves forward and backward.

The clamp part may include a pair of clamp pieces which is openable and closable; a slit may be formed on each distal portion of the clamp pieces which divide the distal portion of the clamp pieces into two; and the ligation part may be openable and closable in the slit.

The insertion tube, the first control shaft member, and the second control shaft member may have flexibility.

A third control mechanism which temporarily closes the pair of arm members via the control tube, may be further included.

Another ligation apparatus for operating a ligation member of the present invention includes: an insertion tube extending toward one direction; a clamp part which is provided on a distal side of the insertion tube and clamps a living organ; a first control mechanism which is connected to the clamp part via a first control shaft member inserted inside the insertion tube and controls opening-and-closing action of the clamp part by advancing and retracting the first control shaft member; a second control mechanism connected to the ligation member which ligates the living organ by closing a pair of arm members, via a second control shaft member inserted inside the insertion tube, which closes the pair of arm members and releases the ligation member by advancing and retracting the second control shaft member.

A control tube inserted inside the insertion tube may be further included, and the second control shaft member may be inserted inside the control tube so that the second control shaft member freely moves forward and backward.

The clamp part may include a pair of clamp pieces which is openable and closable; a slit may be formed on each distal portion of the clamp pieces which divide the distal portion of the clamp pieces into two; and the ligation member may be openable and closable in the slit.

The insertion tube, the first control shaft member, and the second control shaft member may have flexibility.

A third control mechanism which temporarily closes the pair of arm members via the control tube, may be further included.

DETAILED DESCRIPTION OF THE INVENTION

One embodiment of the present invention will be explained below referring to FIGS. 1 to 9.

Figure 1:
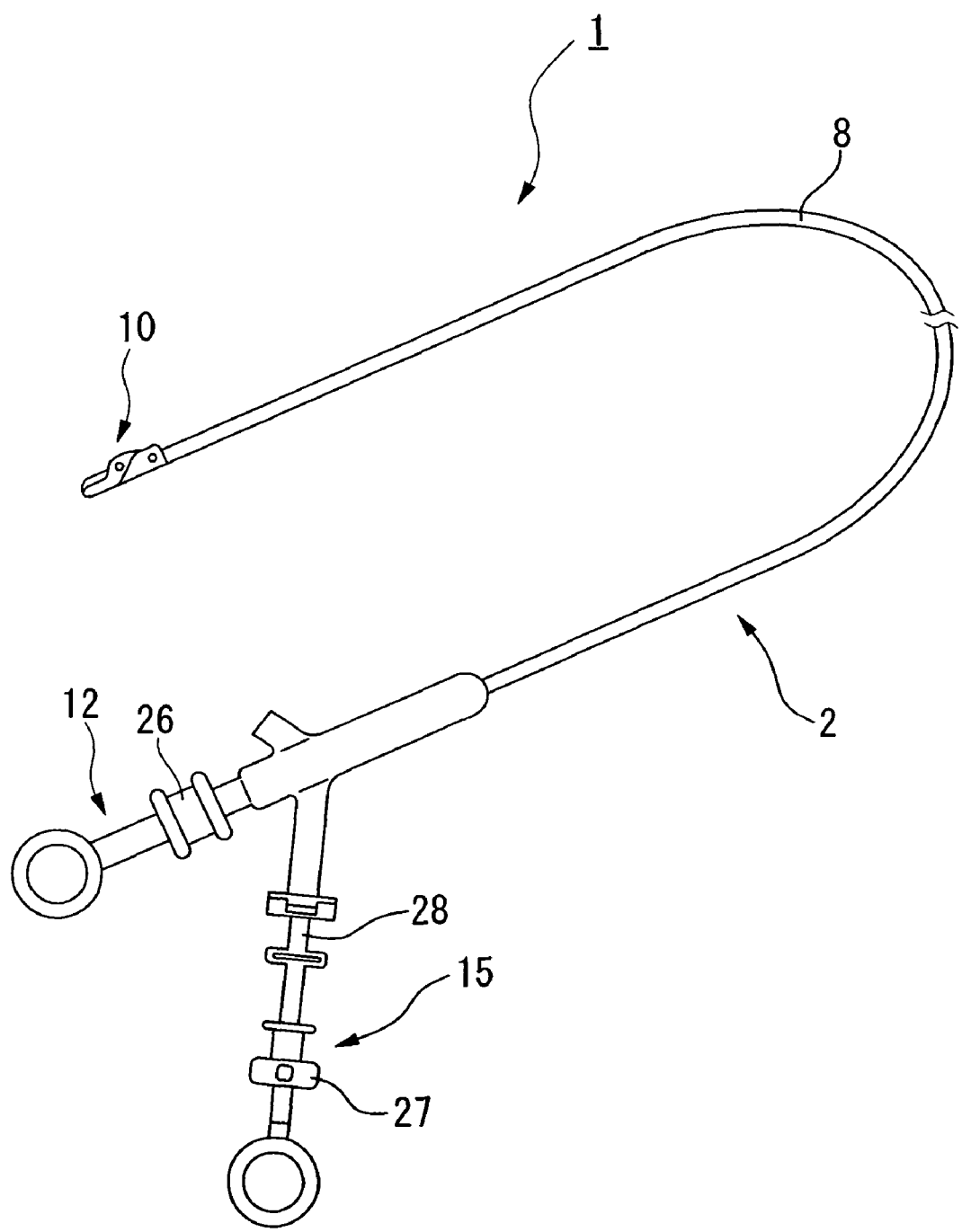
FIG. 1 is a plan view of whole constitution of a ligation apparatus according to one embodiment of the present invention.
Figure 2:
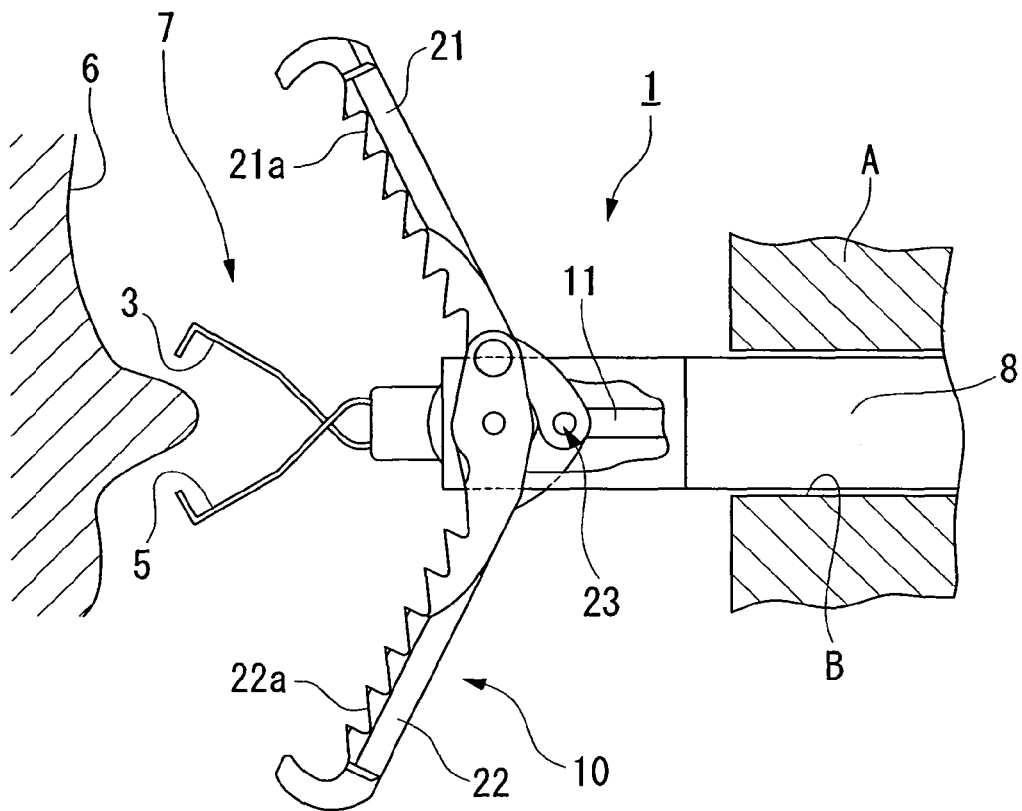
FIG. 2 is a plan view of a distal end of the ligation apparatus.

As shown in FIGS. 1 and 2, a ligation apparatus 1 according to the present invention is used by inserting it into a canal B for treatment tools of a flexible endoscope A. The ligation apparatus 1 is provided with a ligation apparatus main body 2 and a cartridge type of clip unit (ligation part, ligation member) 7 which is attached on the ligation apparatus main body 2 so that it can be freely attached and removed, and ligates an affected part 6 by closing a pair of arm members 3 and 5 facing each other.

The ligation apparatus main body 2 is provided with: an insertion 8 tube extending toward one direction; a clamp part 10 which is provided on a distal side of the insertion tube 8 having a pair of clamp pieces 21 and 22 facing each other, and clamps the affected part 6; and a first control mechanism 12 which is connected to the clamp part 10 via a first control shaft member 11 inserted inside the insertion tube 8 and controls opening-and-closing action of the clamp part 10 by advancing and retracting the first control shaft member 11.

Figure 3:
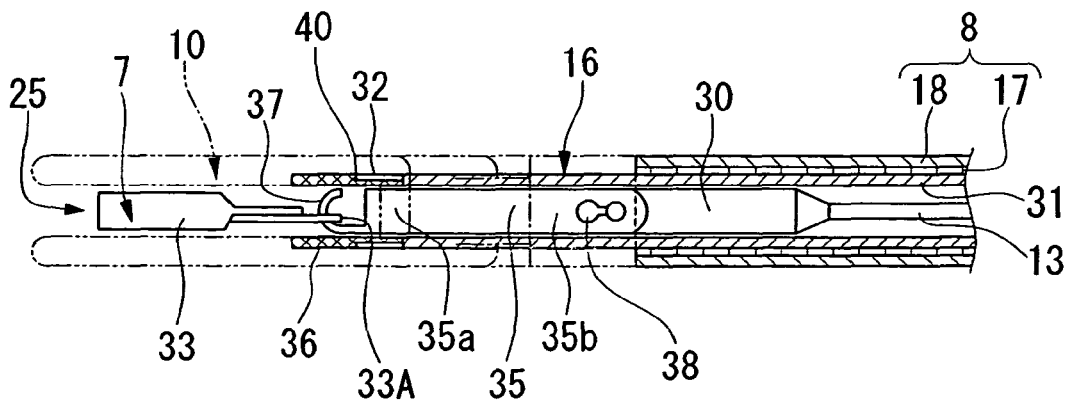
FIG. 3 is a cross sectional view of the distal end of the ligation apparatus.

The ligation apparatus 2 is provided with a second control mechanism 15 connected to the clip unit 7 via a second control shaft member 13 inserted inside the insertion tube 8 as shown in FIG. 3, which closes the pair of arm members 3 and 5 and releases the clip unit 7 by advancing and retracting the second control shaft member 13.

The ligation apparatus main body 2 is further provided with a control tube 16 inserted inside the insertion tube 8; and the second control shaft member 13 is inserted inside the control tube 16 so that the second control shaft member 13 freely moves forward and backward.

The insertion tube 8 is provided with: a flexible insertion tube main body 17 having a short-wind-pitch coil made of a steel wire; and a covering member 18 covering the periphery of the insertion tube main body 17.

Figure 4:
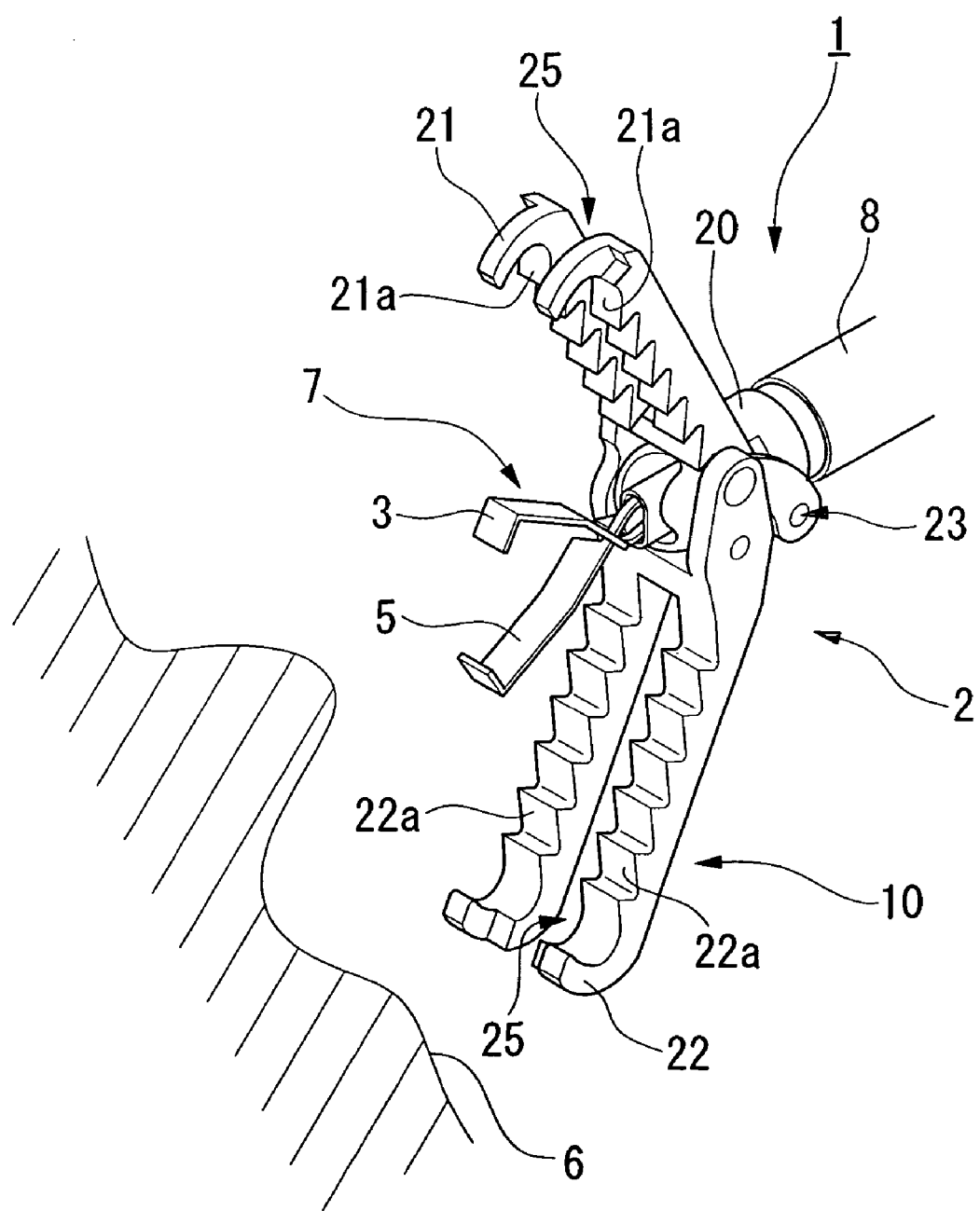
FIG. 4 is a perspective view of the distal end of the ligation apparatus.

As shown in FIG. 4, the clamp part 10 is provided with: a tubular-shaped distal cover 20 connected to the distal end of the insertion tube 8; a pair of clamp pieces 21 and 22 provided on a tip end of the distal cover 20 which faces each other and is openable and closable; and a link mechanism 23 which transfers advancing and retracting operation of the first control shaft member 11 to opening-and-closing operation of the pair of clamp pieces 21 and 22.

The pair of clamp pieces 21 and 22 is made of generally rod-shaped metal members each divided into two extending from a bottom end to a distal end. A slit 25 is formed on each distal side of the pair of clamp pieces 21 and 22. Each of the pair of clamp pieces 21 and 22 has one of corrugated clamp faces 21a and 22a which clamp the affected part 6.

As shown in FIGS. 1 and 2, the first control mechanism 12 is provided with a first slider 26 connected to a bottom end of the first control shaft member 11. The advancing and retracting operation of this first slider 26 is transmitted to the advancing and retracting operation along the axis of the first control shaft member 11, and this action along the axis of the control shaft member 11 is then transferred to opening-and-closing action of the clamp part 10 by the link mechanism 23.

As shown in FIGS. 1 and 3, the second control mechanism 15 is provided with a second slider 27 connected to a bottom end of the second control shaft member 13, and a third slider 28 connected to a bottom end of the control tube 16. The advancing and retracting action of the control tube 16 is made by advancing and retracting action of each second slider 27 and third slider 28.

Each of the second slider 27 and the third slider 28 is operable independently.

The first control shaft member 11 and the second control shaft member 13 are made of, for example, a flexible steel wire. As shown in FIG. 3, a hook 30 for joining the clip unit 7 so that the clip unit 7 can be freely attached and removed, is provided on the distal end of the second control shaft member 13.

The control tube 16 is provided with: a flexible control tube main body 31 having a short-wind-pitch coil made of a steel wire; and a short tube 32 provided on the distal end of the control tube main body 31.

As shown in FIG. 3, the clip unit 7 is provided with a clip 33, a connection plate 35 as a connection member for connecting to the clip 33 so that the clip 33 can be freely attached and removed, and a fastener ring 36 for ligating the affected part 6 using the clip 33.

Figure 5:
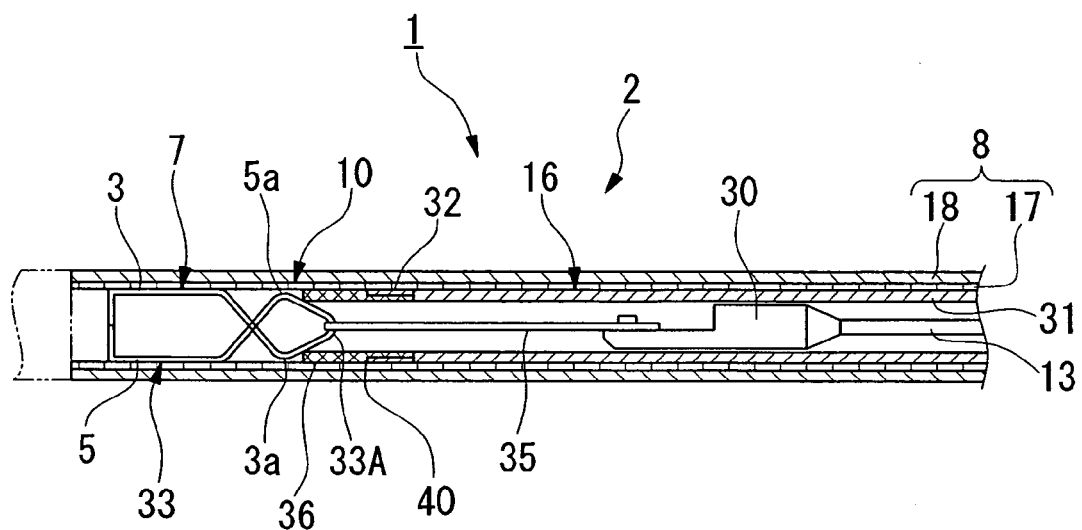
FIG. 5 is a cross sectional view of a clip of the ligation apparatus inserted in an insertion tube.

The clip 33 is made by folding a thin and band-shaped steel plate at its center portion, and then by making this folded portion as a bottom end portion 33A. As shown in FIG. 5, a pair of movable inserted portions 3a and 5a having a pitch between them wider than an internal diameter of the fastener ring 36, is extending from the bottom end portion 33A. Furthermore, a pair of arm members 3 and 5 extending from the pair of movable inserted portions 3a and 5a toward the distal side of the clip 33 is formed. The clip 33 is folded so that the pair of arm members 3 and 5 faces each other, and so that the pair of arm members 3 and 5 will have a function of normally maintaining an opened state.

The connection plate 35 is made of a metal thin plate, and on its one end 35a, a J-shaped hook 37 which can be connected to and be released away from the bottom end 33A of the clip 33, is formed. A joint hole 38 for connecting the hook 30 is formed on another end 35b.

The fastener ring 36 is placed at a position where it covers periphery of the bottom end portion 33A. The fastener ring 36 is formed so that the outer diameter at bottom side is smaller than the inner diameter of the short tube 32, while the outer diameter at a distal side is larger than the inner diameter of the short tube 32, and thus a step 40 is formed at boundary therebetween. Therefore, the step 40 and an end face of the short tube 32 will be joined when the clip unit 7 is installed.

Next, use of the ligation apparatus 1 according to the present invention having the above-mentioned constitution will be explained below.

At first, the clip unit 7 is attached to the second control shaft member 13. At this time, the control tube 16 is extruded in advance from the insertion tube 8 toward distal direction by advancing the third slider 28.

Next, the second control shaft member 13 is forwarded by advancing the second slider 27, and then the hook 30 is extruded toward the distal direction.

Next, by inserting the hook 30 into the joint hole 38 of the clip 33, and then by drawing the second control shaft member 13 into the control tube 16 again by retracting the second slider 27, the distal end of the short tube 32 and the step 40 are joined to each other, and then the clip unit 7 is joined to the distal end of the control tube 16.

Furthermore, the control tube 16 is drawn into the insertion tube 8 when the second control shaft member 13 is pulled backward by retracting the third slider 28. Accordingly, the pair of arm members 3 and 5 is pushed inwardly, and are then closed. As a result, as shown in FIG. 5, the clip unit 7 is installed in the insertion tube 8. At this time, the direction of the clip 33 is adjusted so that the pair of arm members 3 and 5 can open and close in the slits 25 each formed in the pair of clamp pieces 21 and 22.

Next, the insertion tube 8 is inserted into the canal B for treatment tools of the flexible endoscope A after closing the pair of clamp pieces 21 and 22 by operating the first slider 26. Then, the insertion tube 8 is inserted into a body cavity together with the flexible endoscope A.

Next, ligation treatment will be performed.

At first, the distal end of the clamp part 10 is placed close to the affected part 6, and then the second control shaft member 13 is forwarded by operating the second slider 27, and then the clip unit 7 is extruded from inside of the insertion tube 8 toward the outside and the distal direction of the insertion tube 8. At this time, the pair of arm members 3 and 5 will open in the slits 25 because the pair of arm members 3 and 5 of the clip 33 has a function of maintaining an opened state.

Figure 6:
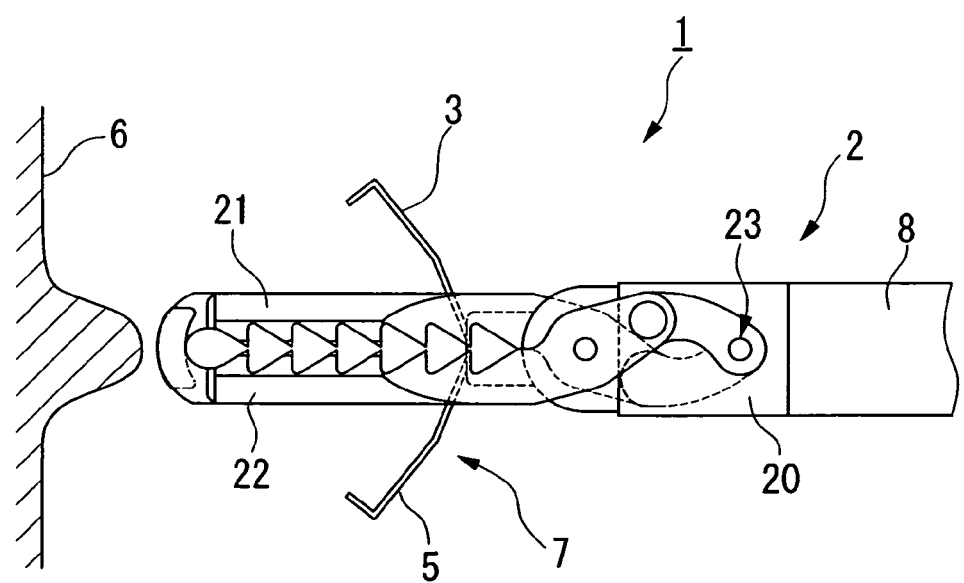
FIG. 6 is a plan view of the clip of the ligation apparatus in the opened state.

Next, the second control shaft member 13 is drawn into the control tube 16 by retracting the second slider 27. Then, the clip 33 is drawn into the fastener ring 36 collapsing the pair of movable inserted portions 3a and 5a because the step 40 of the fastener ring 36 is fixed at the end face of the short tube 32 and the fastener ring 36 does not move. As a result, as shown in FIG. 6, maximum opening of the pair of arm members 3 and 5 will be obtained.

Figure 7:
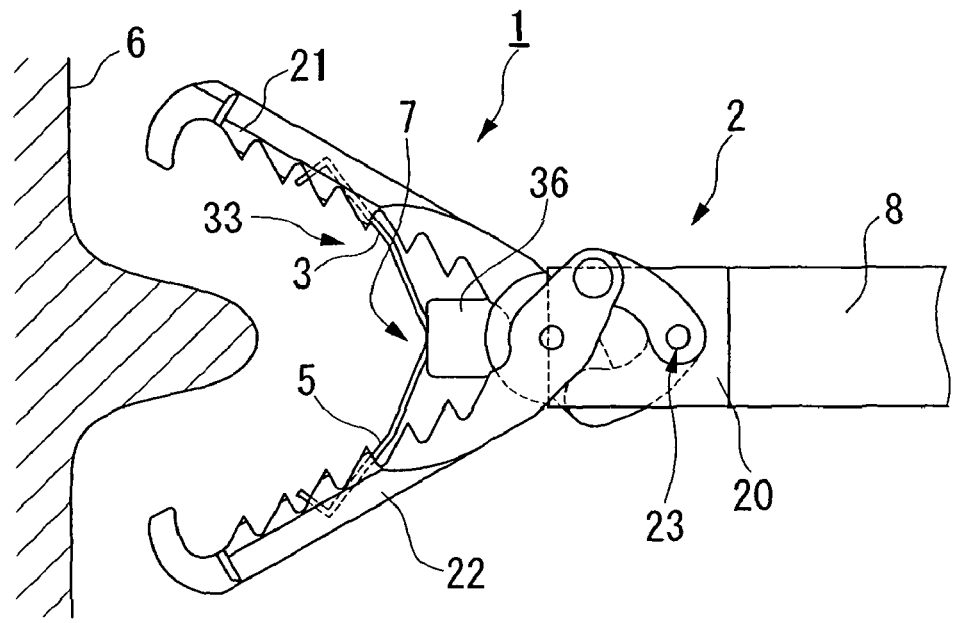
FIG. 7 is a plan view of the clip and clamp pieces of the ligation apparatus, both in the opened state.

At this state, the pair of clamp pieces 21 and 22 is opened via the link mechanism 23 as shown in FIG. 7 by advancing the first control shaft member 11 by advancing the first slider 26.

Figure 8:
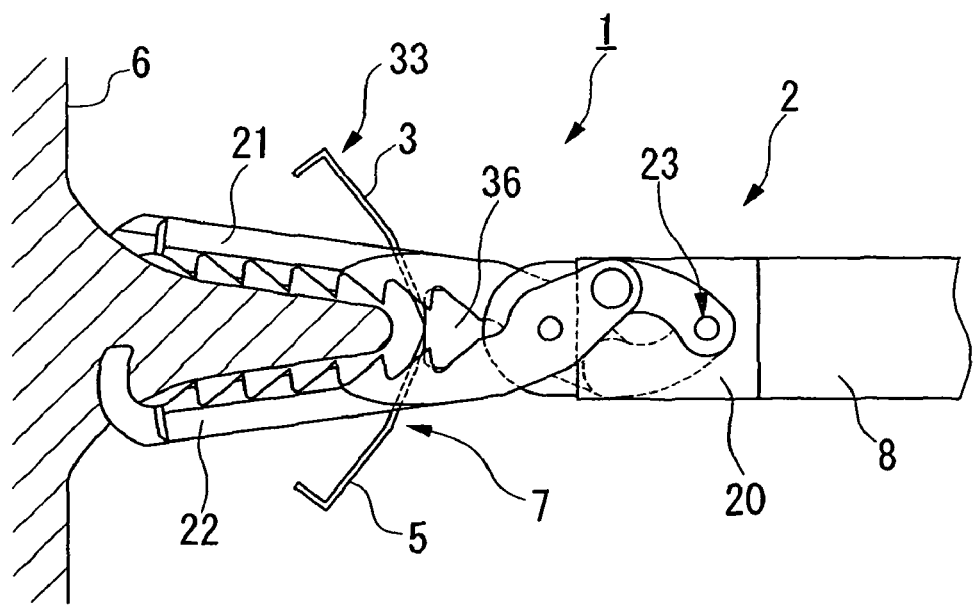
FIG. 8 is a plan view showing the clamp pieces of the ligation apparatus clamping an affected part.

Then, as shown in FIG. 8, the affected part 6 is clamped by closing the pair of clamp pieces 21 and 22 via the link mechanism 23 by retracting the first control shaft member 11 by retracting the first slider 26 backwardly again so that the pair of arm members 3 and 5 can ligate the desired location of the affected part 6.

At this time, as the pair of arm members 3 and 5 maintains an opened state in the slit 25, the pair of clamp pieces 21 and 22 can clamp the desired location by repeating the above-mentioned operations in the case in which the pair of clamp pieces 21 and 22 clamped another location which is offset from the desired location.

Figure 9:
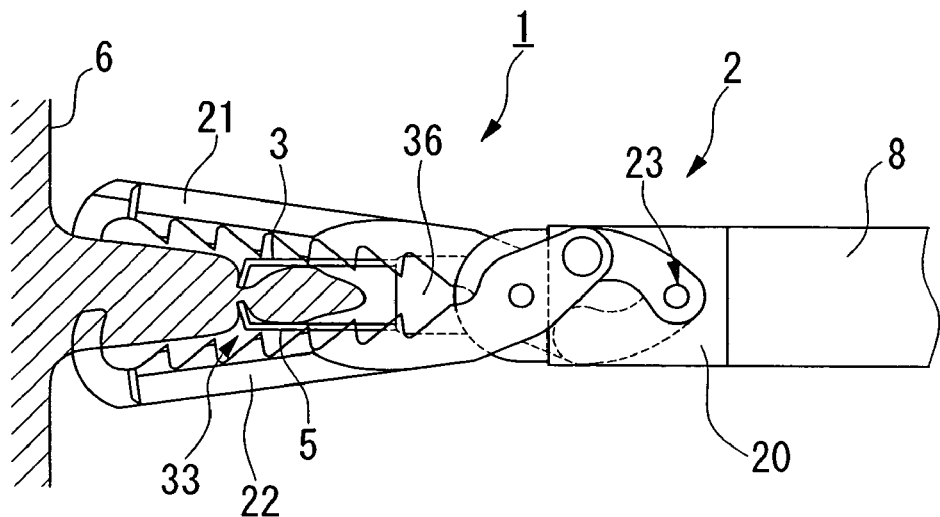
FIG. 9 is a plan view showing the clip in the closed state, clamping the affected part by the clamp pieces of the ligation apparatus.

After fixing the pair of clamp pieces 21 and 22 at the desired location, the second control shaft member 13 is drawn into the control tube 16 by further retracting the second slider 27 toward the bottom side. Then the pair of arm members 3 and 5 of the clip 33 is drawn into the fastener ring 36 and is then closed, and thus the affected part 6 will be clamped as shown in FIG. 9.

In this state, by further retracting the second control shaft member 13, the fastener ring 36 clamping the pair of arm members 3 and 5 will be fixed, and then a reaction force will extend the hook 37 of the connection plate 35, and then the clip 33 will be cut and released from the connection plate 35 together with the fastener ring 36.

Figure 10:
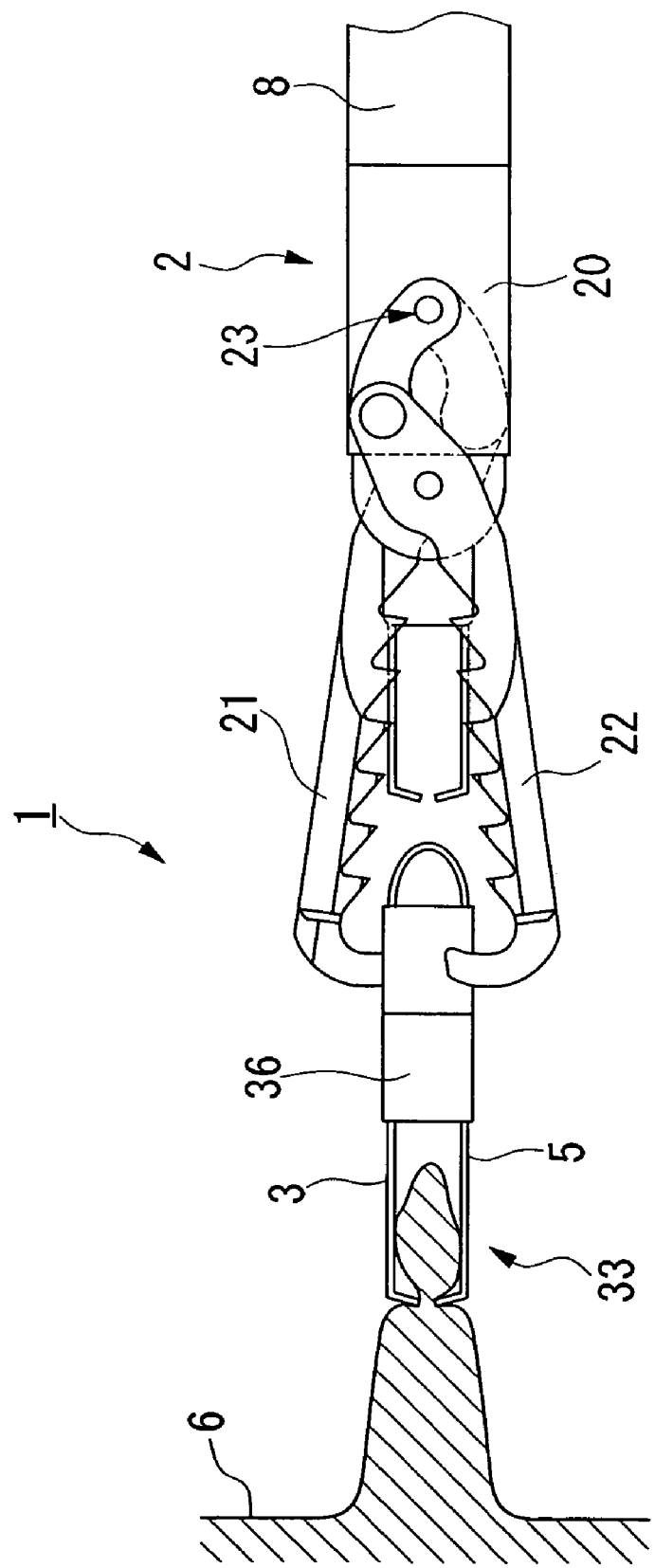
FIG. 10 is a plan view showing the clip of the ligation apparatus which ligates the affected part and is released from a main body of the ligation apparatus.

As a result, as shown in FIG. 10, the clip 33 clamping the affected part 6 will be left in the body cavity.

According to the above-mentioned ligation apparatus 1, each of clamping by the clamp part 10 and ligation by the clip 33 can be done independently by advancing and retracting operation of the first slider 26, the second slider 27 and the third slider 28. Therefore, final ligation will be performed by closing the pair of arm members 3 and 5 by operating the second control shaft member 13, after determining the location to be ligated, by clamping the affected part 6 to be ligated using the pair of clamp pieces 21 and 22 by operating the first control shaft member 11. In addition, it is possible to install the clip 33 on a desired location after clamping the correct position on the affected part 6 because the reattempt of clamping by operating the clamp part 10 via the first control shaft member 11 is possible.

In addition, as the slits 25 which allow opening and closing of the pair of arm members 3 and 5 are formed in the pair of clamp pieces 21 and 22, opening-and-closing operation of the pair of arm members 3 and 5 can be performed in the slits 25. Furthermore, such operation can be performed without interference with opening-and-closing action of the pair of clamp pieces 21 and 22 each other. Therefore, the pair of arm members 3 and 5 can be operated, clamping the affected part 6 using the pair of clamp pieces 21 and 22. At this time, the pair of arm members 3 and 5 can perform ligation treatment at the center position of the desired affected part 6 clamped by the pair of clamp pieces 21 and 22, thus more precise ligation treatment becomes possible.

Moreover, technical features of the present invention are not limited only by the above-mentioned embodiments, and a variety of modifications can be made without departing from the spirit or scope of the present invention.

For example, while the ligation apparatus 1 of the present invention is used together with the flexible endoscope, the ligation apparatus 1 may be used together with a hard endoscope.

Figure 11:
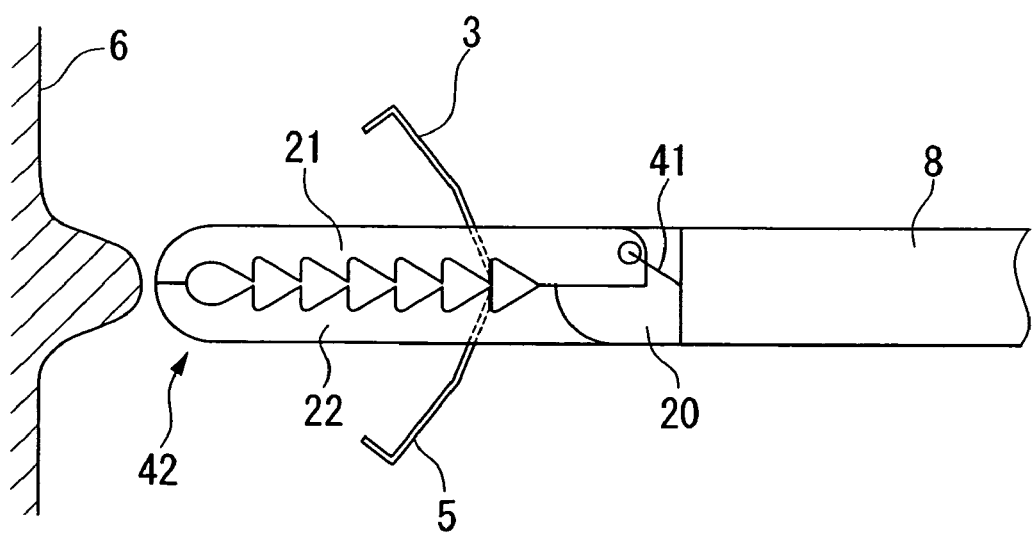
FIG. 11 is a plan view of the clamp pieces of the ligation apparatus.

In addition, the clamp part 10 is not only limited to a constitution having the pair of clamp pieces 21 and 22 which is openable and closable via the link mechanism 23. Instead of this, as shown in FIG. 11, a clamp part 42 having a first control shaft member 41 directly connected to the pair of clamp pieces 21 and 22 may be adopted. In this case, the pair of arm members 3 and 5 having the function of normally maintaining an opened state, may be opened and closed by advancing and retracting them under the condition that the bottom parts of the pair of arm members 3 and 5 contact with the inner surface of the insertion tube 8 at the distal portion.

Figure 12:
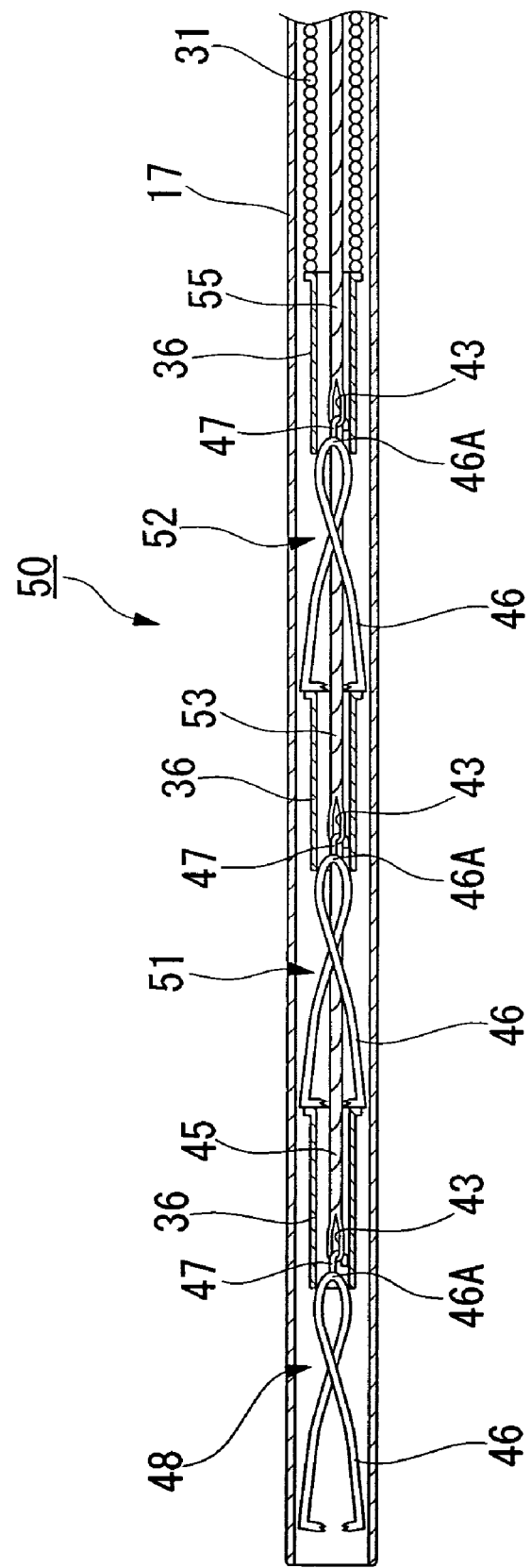
FIG. 12 is a cross sectional view of a distal portion of a ligation apparatus according to another embodiment.

Furthermore, as shown in FIG. 12, a ligation apparatus 50 may be adopted which is provided with: a second control shaft member 45 having, for example, a loop-shaped wire 43 made of a metal torsion wire instead of the hook 30; and three (for example) clip units 48 arranged in series in the insertion tube main body 17, each of the clip units 48 has a J-shaped hook 47 formed at a bottom portion 46A of a clip 46 instead of the clip 33, and is joined with the second control shaft member 45 so that the clip unit 48 can be connected or disconnected with the second control shaft member 45.

In this ligation apparatus 50, the clip units 48, 51, and 52 are arranged in order from the distal side of the insertion tube main body 17. The clip unit 48 is joined with the second control shaft member 45, and the clip unit 51 is joined with the second control shaft member 53, and the clip unit 52 is joined with the second control shaft member 55.

The second control shaft member 45 is placed so that it passes through the fastener rings 36 of the clip units 51 and 52, and the second control shaft member 53 is placed so that it passes through the fastener ring 36 of the clip unit 52. The fastener rings 36 of the clip units 48 and 51 which are different from the short tube 32 provided in the control tube 16, are each joined with the distal ends of the clip units 51 and 52.

This ligation apparatus 50 will have the same action and effect as described in the above-mentioned embodiment.

That is, the affected part 6 can be firmly ligated by closing the clip unit 48 by retracting operation of the second control shaft member 45 after clamping the affected part 6 with the pair of clamp pieces 21 and 22 by controlling the first control shaft member 11. In addition, ligation of plural locations on the affected part or the different plural affected parts can be performed continuously by repeating clamping of the affected part using the pair of clamp pieces 21 and 22 and by performing ligation treatment using the clip unit 52 by retracting operation of the second control shaft member 55, after clamping the affected part using the pair of clamp pieces 21 and 22 and performing ligation treatment using the clip unit 51 by retracting operation of the second control shaft member 53.

Figure 13:
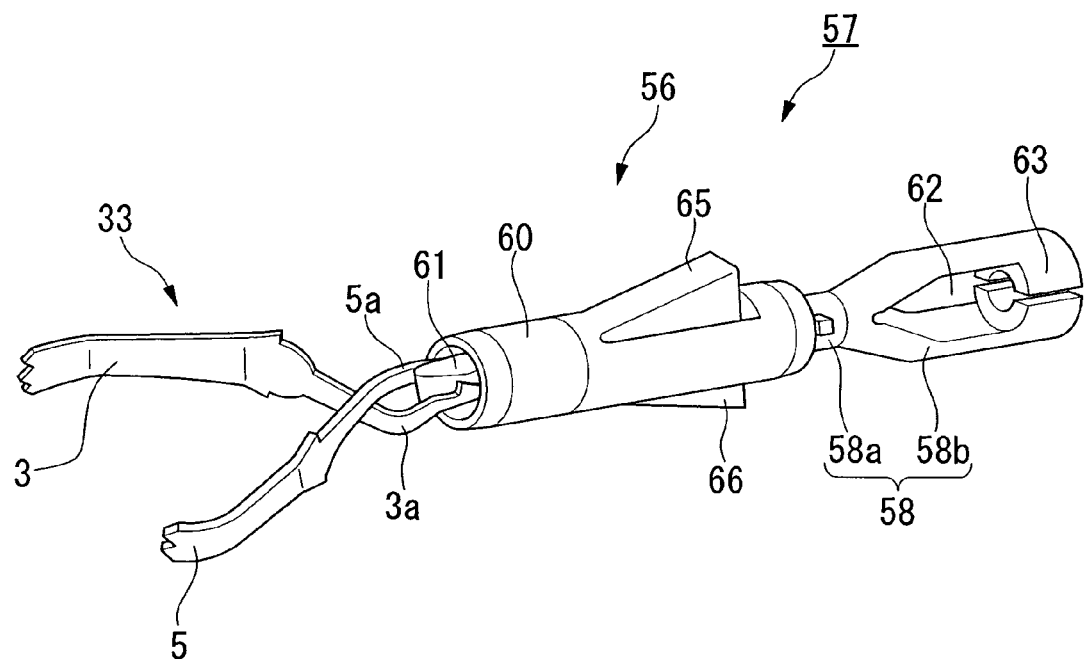
FIG. 13 is a perspective view of a clip unit of the ligation apparatus.

Furthermore, a ligation apparatus 57 utilizing a clip unit 56 shown in FIG. 13 may be adopted.

The clip unit 56 is provided with the above-mentioned clip 33, connection member 58 substantially having a rod shape, and a fastener ring 60. One end portion 58a of the connection member 58 is formed so that the end portion 58a has a smaller outer diameter than another end portion 58b, and a protruding portion 61 which joins with the clip unit 56 is arranged at the distal end. A holding portion 63 having a notch 62 formed by dividing the holding portion 63 into two, is formed on another end portion 58b. On the periphery of the fastener ring 60, a pair of protruding-and-extracting wings 65 and 66 is formed in tapered shape so that the width dimension gradually increases from the distal side to the bottom side, and is freely protruded and extracted.

Figure 14:
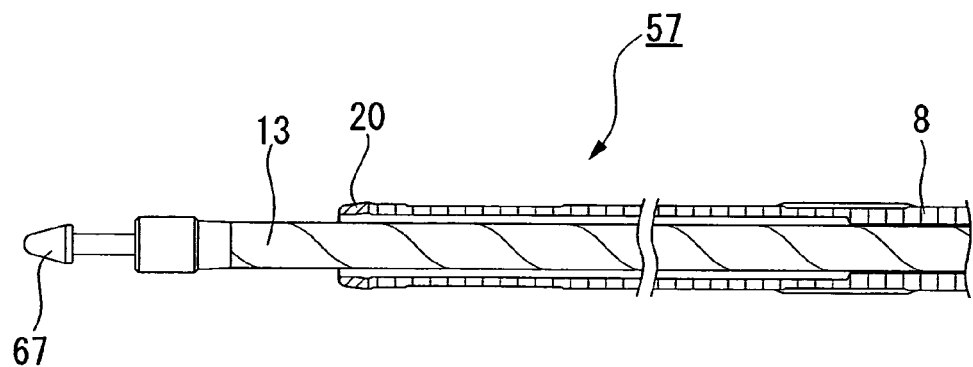
FIG. 14 is a cross sectional view of a part of a distal portion of the ligation apparatus.
Figure 15A:
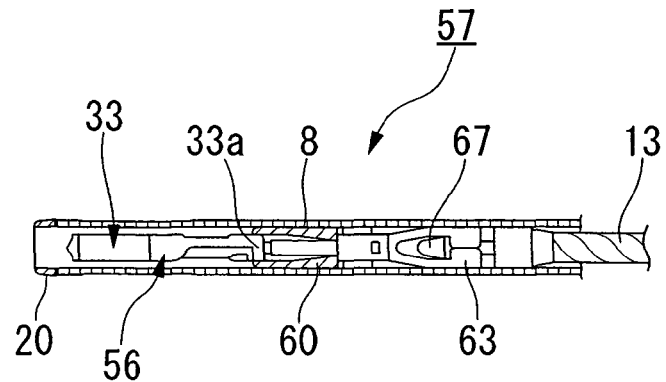
FIGS. 15A to 15C are side views showing extrusion action of the clip unit from the distal portion of the ligation apparatus.

As shown in FIGS. 14 and 15A, an arrowhead-shaped hook 67 is provided on the distal end of the second control shaft member 13. The arrowhead-shaped hook 67 has a distal end formed in conical shape, and connects between the clip unit 56 and the second control shaft member 13 by joining with the holding member 63.

Moreover, the ligation apparatus 57 does not have a part corresponding to the control tube 16, and the second control shaft member 13 is arranged in the insertion tube 8.

This ligation apparatus 57 will also have the same action and effect as described in the above-mentioned embodiment.

Figure 15B:
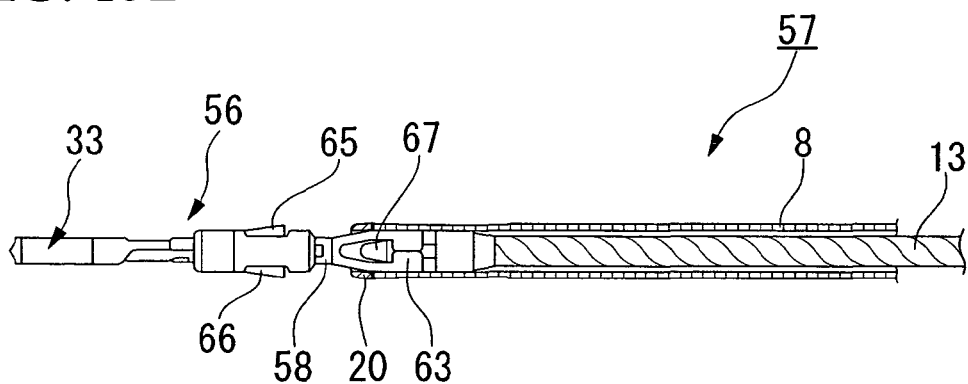
Figure 16A:
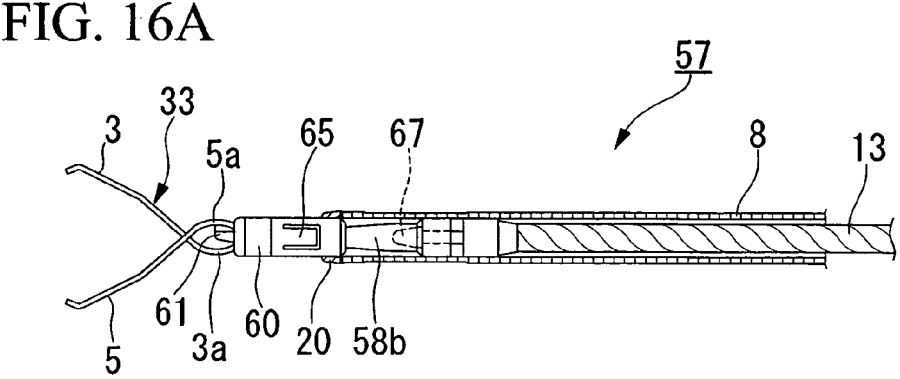
FIGS. 16A to 16D are plan views showing opening-and-closing action of the clip unit of the ligation apparatus.

That is, the clip unit 56 is protruded from inside to the distal side of the insertion tube 8 as shown in FIG. 15B by advancing the second control shaft member 13 toward the distal side. At this time, contact between the pair of protruding-and-extracting wings 65 and 66 and an inner surface of the insertion tube 8 is canceled. Thus, the pair of protruding-and-extracting wings 65 and 66 protrudes in a diametrical direction of the distal cover 20, and then the pair of arm members 3 and 5 is opened as shown in FIG. 16A.

Figure 15C:
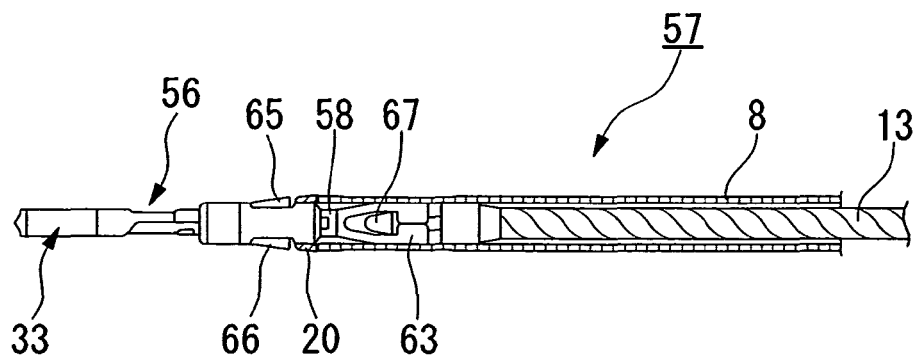

Next, by retracting the second control shaft member 13 toward the bottom end side, the bottom end side faces of the pair of protruding-and-extracting wings 65 and 66 contact with the end face of the distal cover 20 as shown in FIG. 15C, and are temporally stopped.

Figure 16B:
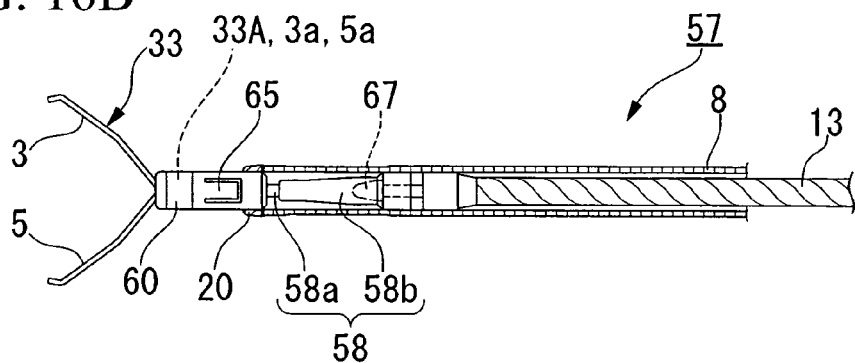

By further retracting the second control shaft member 13 toward the bottom end side, as shown in FIG. 16B, a bottom end 33A of the clip 33 and the pair of movable inserted portions 3a and 5a are drawn into the fastener ring 60 together with the connection member 58 under the condition in that the fastener ring 60 is joined with the distal cover 20 by the pair of protruding-and-extracting wings 65 and 66. Then maximum opening of the pair of arm members 3 and 5 can be obtained.

In this condition, the affected part 6 is clamped by the pair of clamp pieces 21 and 22 by retracting control of the first control shaft member 11.

Figure 16C:
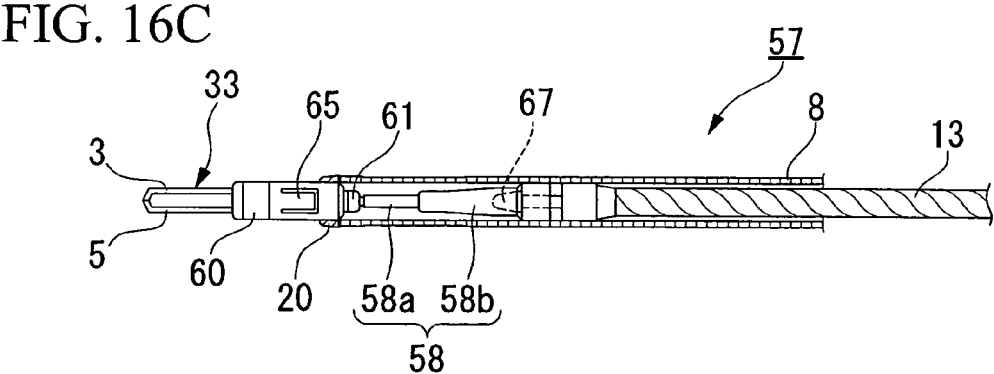

Next, by clamping the affected part 6 and then by drawing the second control shaft member 13 again, the pair of arm members 3 and 5 is drawn into the fastener ring 60 and is closed as shown in FIG. 16C.

Figure 16D:
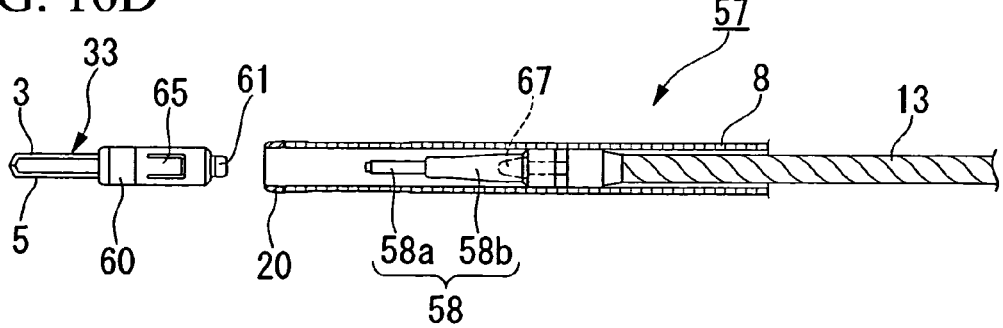

By drawing the second control shaft member 13 furthermore, as shown in FIG. 16D, the connection member 58 breaks on its axial direction, and connection between the clip 33 and the second control shaft member 13 will be discontinued. Then the clip 33 clamping the affected part is released from the ligation apparatus 57 and is allowed to remain in a body.

As explained above, the ligation apparatus of the present invention adopts a constitution including: an insertion tube extending toward one direction; clamp part which is provided on a distal side of the insertion tube and clamps a living organ; a first control mechanism which is connected to the clamp part via a first control shaft member inserted inside the insertion tube and controls opening-and-closing action of the clamp part by advancing and retracting the first control shaft member; a ligation part which ligates the living organ by closing a pair of arm members provided on the distal side of the insertion tube; and a second control mechanism connected to the ligation part via a second control shaft member inserted inside the insertion tube, which closes the pair of arm members and releases the ligation part by advancing and retracting the second control shaft member.

According to this constitution, the clamp part and the ligation part can be controlled independently by the first control mechanism and the second control mechanism. Therefore, a portion to be ligated can be determined by clamping the living organ to be ligated using the clamp part via the first control shaft member by controlling the first control mechanism. Then, ligation can be performed by closing the arm members of the ligation part by controlling the second control mechanism via the second control shaft member.

In addition, the ligation part can be fixed to a desired position clamping an exact position using the clamp part because the clamp part can perform retry clamping by controlling the first control shaft member.

Therefore, according to the ligation apparatus of the present invention, a portion to be ligated can be determined by retrying clamping over and over by the clamp part before ligation using the ligation part. When the ligation treatment is performed, the ligation can be done, clamping the desired position firmly.

In the ligation apparatus, it is preferable that a control tube inserted inside the insertion tube be further included; and the second control shaft member is inserted inside the control tube so that the second control shaft member freely moves forward and backward.

In this case, control without interference between the first control shaft member and the second control shaft member each other can be performed by separating the second control shaft member from the first control shaft member by the control tube.

It is preferable that the clamp part includes a pair of clamp pieces which is openable and closable; a slit is formed on each distal portion of the clamp pieces which divide the distal portion of the clamp pieces into two; and the ligation part is openable and closable in the slit.

In this case, opening-and-closing action of the ligation part can be performed in the slit without interference with opening-and-closing action of the clamp part with each other. In addition, more precise ligation treatment can be performed because the ligation part can ligate the center position of the desired living organ clamped by the clamp part.

It is preferable that the insertion tube, the first control shaft member, and the second control shaft member have flexibility.

In this case, the ligation apparatus can be used for inserting it into a canal for treatment tools of a flexible endoscope, and thus ligation treatment using the flexible endoscope can be performed firmly.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A ligation apparatus including a ligation member which includes a clip and a fastener, the ligation apparatus comprising:
   an insertion tube extending toward one direction;
   a clamp part which is provided on a distal side of the insertion tube, the clamp part including a pair of clamp pieces which are openable and closable, and the clamp part being adapted to clamp a living organ;
   a first control mechanism connected to the clamp part via a first control shaft member inserted inside the insertion tube, which controls opening-and-closing action of the clamp part by advancing and retracting the first control shaft member;
   the ligation member which is provided on the distal side of the insertion tube and adapted to ligate the living organ by closing a pair of arm members of the clip by the fastener;
   a second control mechanism connected to the clip of the ligation member via a second control shaft member inserted inside the insertion tube, which controls opening-and-closing action of the pair of arm members of the clip and releasing action of the clip together with the fastener by advancing and retracting the second control shaft member; and
   a connection part which detachably connects between the clip of the ligation member and the second control shaft member, so as to be able to transfer both of an advancing force and a retracting force of the second control shaft member to the clip of the ligation member, wherein:
   the pair of arm members of the clip is openable and closable, and
   each of the clamp pieces having a passing section therein such that when the clamp pieces are closed, the pair of arm members of the clip can open and close and pass through the passing section, and wherein:
   when the second control shaft member is advanced, the clip of the ligation member opens;
   when the second control shaft member is retracted, the clip of the ligation member is closed by the fastener; and
   when the second control shaft member is further retracted after closing the clip of the ligation member, the clip is released together with the fastener from the second control shaft member.

2. The ligation apparatus according to claim 1, further comprising a control tube inserted inside the insertion tube, wherein the second control shaft member is inserted inside the control tube so that the second control shaft member freely moves forward and backward.

3. The ligation apparatus according to claim 1, wherein the passing section is a slit which is formed on each distal portion of the clamp pieces so as to divide the distal portion of the clamp pieces into two.

4. The ligation apparatus according to claim 1, wherein the insertion tube, the first control shaft member, and the second control shaft member have flexibility.

5. The ligation apparatus according to claim 2, further comprising a third control mechanism which temporarily closes the pair of arm members via the control tube.

6. A ligation apparatus for operating a ligation member which includes a clip and a fastener, the ligation apparatus comprising:
   an insertion tube extending toward one direction;
   a clamp part which is provided on a distal side of the insertion tube, the clamp part including a pair of clamp pieces which are openable and closable, and the clamp part being adapted to clamp a living organ;
   a first control mechanism connected to the clamp part via a first control shaft member inserted inside the insertion tube, which controls opening-and-closing action of the clamp part by advancing and retracting the first control shaft member;
   a second control mechanism connected to the clip of the ligation member which is adapted to ligate the living organ by closing a pair of arm members of the clip, via a second control shaft member inserted inside the insertion tube, which controls opening-and-closing action of the pair of arm members of the clip and releasing action of the clip together with the fastener by advancing and retracting the second control shaft member; and
   a connection part which detachably connects between the clip of the ligation member and the second control shaft member, so as to be able to transfer both an advancing force and a retracting force of the second control shaft member to the clip of the ligation member, wherein:
   the pair of arm members of the clip is openable and closable, and
   each of the clamp pieces having a passing section therein such that when the clamp pieces are closed, the pair of arm members of the clip can open and close and pass through the passing section, and wherein:
   when the second control shaft member is advanced, the clip of the ligation member opens;
   when the second control shaft member is retracted, the clip of the ligation member is closed by the fastener; and
   when the second control shaft member is further retracted after closing the clip of the ligation member, the clip is released together with the fastener from the second control shaft member.

7. The ligation apparatus according to claim 6, further comprising a control tube inserted inside the insertion tube, wherein the second control shaft member is inserted inside the control tube so that the second control shaft member freely moves forward and backward.

8. The ligation apparatus according to claim 6, wherein the passing section is a slit which is formed on each distal portion of the clamp pieces so as to divide the distal portion of the clamp pieces into two.

9. The ligation apparatus according to claim 6, wherein the insertion tube, the first control shaft member, and the second control shaft member have flexibility.

10. The ligation apparatus according to claim 7, further comprising a third control mechanism which temporarily closes the pair of arm members via the control tube.

11. A ligation apparatus including a ligation member, the ligation apparatus comprising:
    an insertion tube extending toward one direction;
    a clamp part which is provided on a distal side of the insertion tube, the clamp part including a pair of clamp pieces which are openable and closable, and the clamp part being adapted to clamp a living organ;
    a first control mechanism connected to the clamp part via a first control shaft member inserted inside the insertion tube, which controls opening-and-closing action of the clamp part by advancing and retracting the first control shaft member;
    the ligation member which has a pair of arm members, is provided on the distal side of the insertion tube and is adapted to ligate the living organ by closing the pair of arm members; and
    a second control mechanism connected to the ligation member via a second control shaft member inserted inside the insertion tube, which controls opening-andclosing action of the ligation member by advancing and retracting the second control shaft member, wherein;

each of the clamp pieces having a slit which is formed on the distal portion of the clamp piece so as to divide the distal portion of the clamp piece into two such that when the clamp pieces are closed, the pair of arm members of the ligation member can open and close and pass through the slit.

12. The ligation apparatus according to claim 11, further comprising a control tube inserted inside the insertion tube, wherein the second control shaft member is inserted inside the control tube so that the second control shaft member freely moves forward and backward.

13. The ligation apparatus according to claim 11, wherein the insertion tube, the first control shaft member, and the second control shaft member have flexibility.

* * * * *